(12) United States Patent
Zhao et al.

(10) Patent No.: US 12,057,234 B2
(45) Date of Patent: Aug. 6, 2024

(54) SYSTEM FOR PREDICTING THERAPY RESISTANCE AND ITS MOLECULAR MECHANISMS IN RECTAL CANCER BEFORE TREATMENT

(71) Applicant: CANCER HOSPITAL, CHINESE ACADEMY OF MEDICAL SCIENCES, Beijing (CN)

(72) Inventors: Qing Zhao, Beijing (CN); Xu Guan, Beijing (CN); Enrui Liu, Beijing (CN); Ran Wei, Beijing (CN); Xiaoxiao Song, Beijing (CN)

(73) Assignee: CANCER HOSPITAL, CHINESE ACADEMY OF MEDICAL SCIENCES, Beijing (CN)

( * ) Notice: Subject to any disclaimer, the term of this patent is extended or adjusted under 35 U.S.C. 154(b) by 0 days.

(21) Appl. No.: 18/385,405

(22) Filed: Oct. 31, 2023

(65) Prior Publication Data
US 2024/0062915 A1    Feb. 22, 2024

Related U.S. Application Data

(63) Continuation of application No. PCT/CN2022/114997, filed on Aug. 26, 2022.

(30) Foreign Application Priority Data

Apr. 6, 2022  (CN) .......................... 202210352938.4

(51) Int. Cl.
*G16H 50/70*     (2018.01)
*G06T 11/20*     (2006.01)
(Continued)

(52) U.S. Cl.
CPC ........... *G16H 50/70* (2018.01); *G06T 11/206* (2013.01); *G06V 10/225* (2022.01); *G06V 10/25* (2022.01);
(Continued)

(58) Field of Classification Search
CPC ........ G16H 50/70; G16H 10/60; G16H 30/20; G16H 50/20; G16H 50/30; G16H 30/40;
(Continued)

(56) References Cited

U.S. PATENT DOCUMENTS

2006/0120995 A1    6/2006   Shah
2015/0344964 A1   12/2015   Höfler et al.
(Continued)

FOREIGN PATENT DOCUMENTS

CN    108694718 A    10/2018
CN    109599181 A     4/2019
(Continued)

OTHER PUBLICATIONS

Wang Yang, et al., Progress in the function and mechanism of chemoradiotherapy resistance in colorecal cancer, Tumor, 2017, pp. 795-800, vol. 37.
(Continued)

*Primary Examiner* — Alexander Satanovsky
(74) *Attorney, Agent, or Firm* — Bayramoglu Law Offices LLC

(57) ABSTRACT

A system for predicting therapy resistance and its molecular mechanisms in rectal cancer before treatment is provided. The system includes a feature extraction device, a collection device, a signature construction device and a prediction device. The system can predict responses to neoadjuvant therapy in patients before treatment, analyze patients who are resistant to rectal cancer therapy and their underlying molecular mechanism, thereby enabling personalized therapy for patients who are resistant to rectal cancer therapy. The system has important clinical significance in improving the overall survival of rectal cancer patients.

7 Claims, 5 Drawing Sheets

(51) Int. Cl.
*G06V 10/22* (2022.01)
*G06V 10/25* (2022.01)
*G06V 10/44* (2022.01)
*G06V 10/54* (2022.01)
*G06V 10/766* (2022.01)
*G06V 10/774* (2022.01)
*G06V 20/70* (2022.01)
*G16H 10/60* (2018.01)
*G16H 30/20* (2018.01)

(52) U.S. Cl.
CPC .............. *G06V 10/44* (2022.01); *G06V 10/54* (2022.01); *G06V 10/766* (2022.01); *G06V 10/774* (2022.01); *G06V 20/70* (2022.01); *G16H 10/60* (2018.01); *G16H 30/20* (2018.01); *G06V 2201/03* (2022.01)

(58) Field of Classification Search
CPC ...... G16H 50/50; G16H 70/60; G06T 11/206; G06V 10/225; G06V 10/25; G06V 10/44; G06V 10/54; G06V 10/766; G06V 10/774; G06V 20/70; G06V 2201/03; Y02A 90/10
See application file for complete search history.

(56) References Cited

U.S. PATENT DOCUMENTS

| | | | |
|---|---|---|---|
| 2017/0091409 | A1 | 3/2017 | Jiang |
| 2017/0193175 | A1 | 7/2017 | Madabhushi et al. |
| 2020/0395097 | A1* | 12/2020 | Chang .................... G16B 25/10 |
| 2021/0082540 | A1* | 3/2021 | Buechler ................ G16H 70/60 |
| 2021/0090694 | A1* | 3/2021 | Colley ................... G16H 15/00 |

FOREIGN PATENT DOCUMENTS

| | | |
|---|---|---|
| CN | 111863126 A | 10/2020 |
| CN | 113061655 A | 7/2021 |
| CN | 113610845 A | 11/2021 |
| CN | 113817825 A | 12/2021 |
| CN | 113846164 A | 12/2021 |
| CN | 114664413 A | 6/2022 |
| RU | 2021107011 A | 5/2021 |

OTHER PUBLICATIONS

Adele M. Nicolas, et al., Inflammatory fibroblasts mediate resistance to neoadjuvant therapy in rectal cancer, Cancer Cell, 2022, pp. 168-184, e1-e13, vol. 40.

* cited by examiner

SYSTEM FOR PREDICTING THERAPY RESISTANCE AND ITS MOLECULAR MECHANISMS IN RECTAL CANCER BEFORE TREATMENT

CROSS REFERENCE TO RELATED APPLICATIONS

This application is a continuation application of International Application No. PCT/CN2022/114997, filed on Aug. 26, 2022, which claims priority to Chinese Patent Application No. 202210352938.4, filed on Apr. 6, 2022, the entire contents of both of which are incorporated herein by reference.

TECHNICAL FIELD

The present disclosure relates to technical fields of predicting therapy resistance and its molecular mechanism, and in particular, to a system for predicting therapy resistance and its molecular mechanisms in rectal cancer before treatment.

BACKGROUND

Currently, patients with locally advanced rectal cancer (LARC), may select a comprehensive treatment protocol including preoperative neoadjuvant chemotherapy (NCRT), in combination with total mesorectal excision (TME) surgery and postoperative chemotherapy. However, responses to preoperative NCRT and prognosis in LARC patients vary greatly. According to the tumor regression grade (TRG) standard of neoadjuvant therapy for rectal cancer recommended by American Joint Committee on Cancer (AJCC), less than 50% of LARC patients can achieve a good pathological response, namely TRG 0-1, and obtain an obvious improvement in prognosis; while more than 50% of treatment-insensitive patients, namely TRG 2-3, fail to benefit from NCRT, instead their timing of surgery may be delayed, thereby increasing risks of postoperative complications and progression.

Large-scale molecular expression or genetic testing before treatment requires high testing costs and longer testing time, causing a certain economic burden on patients and the society. Therefore, although the above markers have good predictive performance, it is still difficult to promote and apply them clinically in a large scale. In addition, molecular expression and genetic testing generally require preoperative colonoscopic biopsy to increase the amount of tissue samples, or need to obtain a portion of postoperative resection specimen for testing, the former increases the trauma of testing and risks, and the latter cannot carry out effective intervention before surgery based on the testing results.

SUMMARY OF THE INVENTION

The main purpose of the present disclosure is to provide a system for predicting therapy resistance and its molecular mechanisms in rectal cancer before treatment, aiming to solve the technical problem of poor detection in patients that are insensitive to rectal cancer neoadjuvant therapy in the prior art.

The system for predicting therapy resistance and its molecular mechanisms in rectal cancer before treatment comprises a feature extraction device, a collection device, a signature construction device and a prediction device, wherein,
  the feature extraction device is used to extract features on radiological images and pathological images marked with a region of interest of a patient, thereby obtaining radiomics feature values and pathomics feature values;
  the collection device is used to collect clinical data of patients;
  the signature construction device is used to screen radiomics feature values and pathomics feature values, and then to construct multi-omics signatures characterizing therapy resistance and its molecular mechanisms;
  the prediction device is used to perform regression analysis on the multi-omics signatures characterizing therapy resistance and its molecular mechanisms and the clinical data, and then to display prediction results of therapy resistance and its molecular mechanisms in rectal cancer based on the analysis results.

In an embodiment, the system for predicting therapy resistance and its molecular mechanisms in rectal cancer before treatment further comprises an image preprocessing device.

The image preprocessing device is used to invoke the radiological images having filtered and normalized signal intensity and stained pathological images of rectal biopsy specimens of patients through a preset invoking path.

The image preprocessing device is further used to outline the radiological images and pathological images by ITK-SNAP software and ImageScope software so as to obtain the radiological images and pathological images marked with the region of interest of the patient.

In an embodiment, the feature extraction device is further used to extract features on the radiological images marked with the region of interest of the patient, at least based on first-order features, shape features and texture features for describing a lesion, thereby obtaining radiomics feature values.

The feature extraction device is further used to extract features on the pathological images marked with the region of interest of the patient, at least based on pixel intensity, morphological features and nuclear texture features, thereby obtaining pathomics feature values.

In an embodiment, the collection device is further used to invoke an information collection platform, and to collect information at least comprising gender, age, body mass index, tumor differentiation degree, serological test results, molecular marker testing information and surgical pathological TRG information through the information collection platform.

The collection device is further used to obtain clinical data of patients based on the information comprising gender, age, body mass index, the tumor differentiation degree, serological test results, molecular marker testing information and surgical pathological TRG information.

In an embodiment, the signature construction device comprises a data cleaning module, a logistic regression module, and a signature vector computation module.

The data cleaning module is used to clean multi-omics data of the radiomics feature values and the pathomics feature values, to obtain the multi-omics data that meet the requirements by removing invalid data and erroneous data, and then to convert continuous variables in the multi-omics data into binary variables with the median as threshold, to obtain converted multi-omics data.

The logistic regression module is used to perform dimensionality reduction on the converted multi-omics data based on the relationship between the omics features and the expression variables of the molecular markers, thereby obtaining radiomics features and pathomics features that can characterize the expression levels of the molecular markers and preset state.

The signature vector computation module is used to perform machine learning with the radiomics features and pathomics features that can characterize the expression levels of each molecular marker and preset state to obtain corresponding radiomics feature vectors and pathomics feature vectors, and then to label the corresponding radiomics feature vectors and pathomics feature vectors so as to obtain multi-omics signatures characterizing therapy resistance and its molecular mechanisms.

In an embodiment, the logistic regression module is further used to perform dimensionality reduction on the converted multi-omics data through least absolute shrinkage and selection operator in R-language based on the relationship between the omics features and the expression variables of the molecular markers so as to screen out the radiomics features and pathomics features that can characterize the expression levels of the molecular markers and whether they are in deficient mismatch repair status.

In an embodiment, the logistic regression module is further used to verify the screened radiomics features and pathomics features that can characterize the expression levels of molecular markers and whether they are in deficient mismatch repair status based on the molecular marker testing information and surgical pathological TRG information.

In an embodiment, the prediction device comprises an analysis module, a generation module and a prediction module; wherein,
the analysis module is used to perform a univariable regression analysis on the clinical data and a multiple regression analysis on the multi-omics signatures characterizing therapy resistance and its molecular mechanisms, thereby obtaining clinical factors and molecular typing signatures that affect patient survival;
the generation module is used to learn the clinical factors and molecular typing signatures that affect patient survival through an initial learning model so as to generate a prediction model;
the prediction module is used to predict the presence of therapeutic resistance and its molecular mechanisms based on the input information of rectal cancer from which pathology is to be predicted.

In an embodiment, the analysis module is further used to screen out clinical risk factors affecting sensitivity to therapy resistance in patients by the univariable regression analysis in SPSS software, and to perform the multiple regression analysis on the multi-omics signatures that characterize therapy resistance and its molecular mechanisms using the multiple regression analysis in SPSS software, thereby obtaining clinical factors and molecular typing signatures that can independently affect patient survival.

In an embodiment, the prediction device further comprises a display module.

The display module is used to display prediction results through an alignment diagram, and to display weights of the corresponding molecular typing signatures and probability of therapy resistance to rectal cancer.

The system for predicting therapy resistance and its molecular mechanisms in rectal cancer before treatment according to the present disclosure comprises a feature extraction device, a collection device, a signature construction device and a prediction device; wherein, the feature extraction device is used to extract features on radiological images and pathological images marked with a region of interest of the patient, thereby obtaining radiomics feature values and pathomics feature values; the collection device is used to collect clinical data of patients; the signature construction device is used to screen the radiomics feature values and pathomics feature values, and then to construct multi-omics signatures characterizing therapy resistance and its molecular mechanisms; the prediction device is used to perform regression analysis on the multi-omics signatures characterizing therapy resistance and its molecular mechanisms and the clinical data, and to display prediction results of therapy resistance in rectal cancer and its molecular mechanisms based on the analysis results. The present disclosure could predict responses to neoadjuvant therapy in patients before treatment, analyze patients who are resistant to rectal cancer therapy and their underlying molecular mechanism, thereby enabling personalized therapy for patients who are resistant to rectal cancer therapy. Therefore, it has important clinical significance in improving the overall survival of rectal cancer patients.

The realization of the purposes, functional characteristics and advantages of the present disclosure will be further described in combination with Examples and with reference to the accompanying drawings.

Explanatory notes of reference numbers:

| Reference Number | Name | Reference Number | Name |
| --- | --- | --- | --- |
| 10 | feature extraction device | 40 | prediction device |
| 20 | collection device | 401 | analysis module |
| 30 | signature construction device | 402 | generation module |

-continued

| Reference Number | Name | Reference Number | Name |
| --- | --- | --- | --- |
| 301 | data cleaning module | 403 | prediction module |
| 302 | logistic regression module | 404 | display module |
| 303 | signature vector computation module | 50 | image preprocessing device |

DETAILED DESCRIPTION OF THE EMBODIMENTS

It should be understood that, the specific examples described herein are only used to explain the present disclosure, but not to limit the present disclosure.

Figure 1:
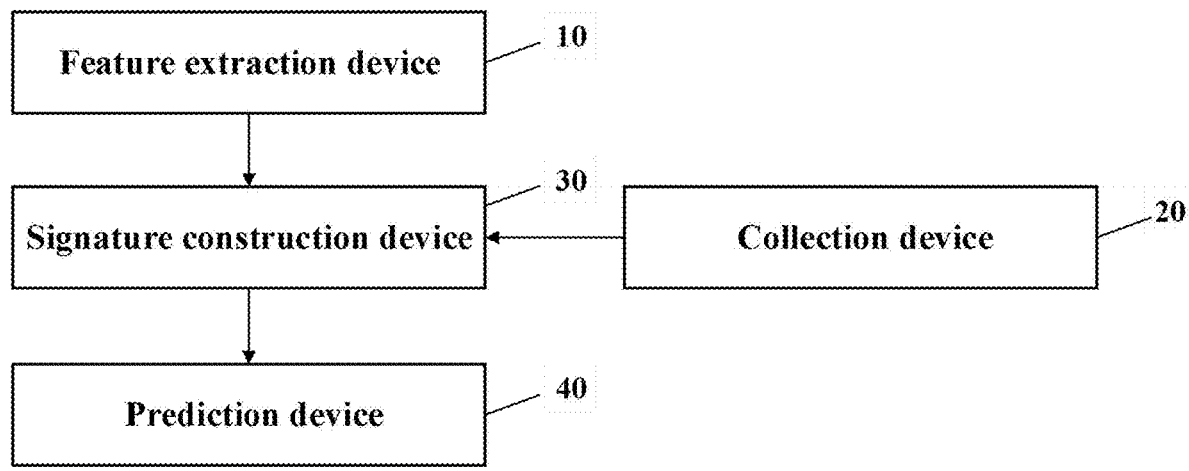
FIG. 1 depicts a block diagram of Example 1 of the system for predicting therapy resistance and its molecular mechanisms in rectal cancer before treatment according to the present disclosure.

Referring to FIG. 1, FIG. 1 is a block diagram of Example 1 of the system for predicting therapy resistance and its molecular mechanisms in rectal cancer before treatment according to the present disclosure.

In Example 1, the system for predicting therapy resistance and its molecular mechanisms in rectal cancer before treatment comprises a feature extraction device 10, a collection device 20, a signature construction device 30, and a prediction device 40; the feature extraction device 10 is used to extract features on radiological images and pathological images marked with a region of interest of the patient, thereby obtaining radiomics feature values and pathomics feature values.

It should be noted that, the subject implementing this example of the present disclosure is a device for predicting therapy resistance and its molecular mechanisms in rectal cancer before treatment, and it could also be other devices or equipments capable of performing the same or similar functions, which are not limited in this example.

In a specific example, the feature extraction device 10 is used to extract features on radiological images and pathological images marked with a region of interest of a patient, the radiological images are magnetic resonance T2-weighted images (T2WI) of rectal magnetic resonance imaging (MM) and images of diffusion-weighted imaging (DWI) sequence, the pathological images are images of rectal biopsy pathological whole slide image (WSI).

In the present example, the collection device 20 is used to collect clinical data of patients. The clinical data of patients are collected by the collection device 20 by means of an information collection platform. The information collection platform can be a computer, a tablet or a mobile terminal, by which operator uploads the clinical data of patients to the information collection platform. When it is necessary to collect the clinical data of patients, the collection device 20 invokes the information collection platform to collect the clinical data of patients through the platform.

Further, the collection device 20 is further used to invoke the information collection platform to collect through the platform at least information comprising gender, age, body mass index, tumor differentiation degree, serological test results, molecular marker testing information and surgical pathological TRG information. The collection device 20 is further used to obtain the clinical data of patients based on the information comprising gender, age, body mass index, tumor differentiation degree, serological test results, molecular marker testing information and surgical pathological TRG information.

It should be understood that, the clinical data of patients include at least information comprising gender, age, body mass index (BMI), tumor differentiation degree, serological test results, molecular marker testing information and surgical pathological TRG information. The serological test results include carcinoembryonic antigen (CEA), carbohydrate antigen-199 (CA-199) levels, etc. The molecular marker testing information include hypoxia inducible factor-1α (HIF-1α), vascular endothelial growth factor (VEGF), immune score obtained by immunohistochemical staining of CD4 (cluster of differentiation) and CD8 factors, and deficient mismatch repair (dMMR) status, etc. Users can upload the clinical data of patients through the information collection platform, and the collection device 20 collects the clinical data of patients by invoking the information collection platform.

In this example, the signature construction device 30 is used to screen the radiomics feature values and pathomics feature values, and then to construct multi-omics signatures characterizing therapy resistance and its molecular mechanisms.

It should be noted that, the signature construction device 30 performs screening mainly based on the radiomics feature values and pathomics feature values extracted by the feature extraction device 10, and constructs signatures on the screened data. Before the construction of signatures, the device 30 uses molecular marker testing information in the clinical data collected by the collection device 20, including HIF-1α, VEGF, immune score obtained by immunohistochemical staining of CD4 (cluster of differentiation) and CD8 factors and deficient mismatch repair (dMMR) status, to verify the screened data, and then constructs signatures on the verified data, thereby obtaining multi-omics signatures characterizing therapy resistance and its molecular mechanisms.

It should be understood that, the prediction device 40 is used to perform regression analysis on the multi-omics signatures characterizing therapy resistance and its molecular mechanisms and the clinical data, and then to display prediction results of therapy resistance and its molecular mechanisms in rectal cancer based on analysis results.

The prediction device 40 performs a multiple regression analysis after receiving the multi-omics signatures characterizing therapy resistance and its molecular mechanisms transmitted by the signature construction device 30, and performs a univariable regression analysis after receiving the clinical data of patients transmitted by the collecting device 20. The device 40 then processes the analyzed multi-omics signatures characterizing therapy resistance and its molecular mechanisms and clinical data, and displays prediction results of therapy resistance and its molecular mechanisms in rectal cancer based on processed results.

In a specific example, SPSS (Statistics 22, IBM Corp, Armonk, NY) is a statistical analysis software. The prediction device 40 performs the univariable regression analysis on clinical data using Univariable Regression Analysis in SPSS (Statistics 22, IBM Corp, Armonk, NY) software, and performs the multiple regression analysis on multi-omics signatures characterizing therapy resistance and its molecular mechanisms using Multiple Regression Analysis in SPSS (Statistics 22, IBM Corp, Armonk, NY) software.

In this example, the system for predicting therapy resistance and its molecular mechanisms in rectal cancer before treatment is configured to include a feature extraction device, a collection device, a signature construction device and a prediction device; the feature extraction device is used to extract features on radiological images and pathological images marked with a region of interest of a patient, thereby obtaining radiomics feature values and pathomics feature values; the collection device is used to collect clinical data of patients; the signature construction device is used to screen the radiomics feature values and pathomics feature values, and then to construct multi-omics signatures characterizing therapy resistance and its molecular mechanisms; the prediction device is used to perform regression analysis on the multi-omics signatures characterizing therapy resistance and its molecular mechanisms and the clinical data, and then to display prediction results of therapy resistance and its molecular mechanisms in rectal cancer based on analysis results. The present disclosure could predict responses to neoadjuvant therapy in patients before treatment, analyze patients who are resistant to rectal cancer therapy and their underlying molecular mechanism, thereby enabling personalized therapy for patients who are resistant to rectal cancer therapy. Therefore, the present disclosure has important clinical significance in improving the overall survival of rectal cancer patients.

Figure 2:
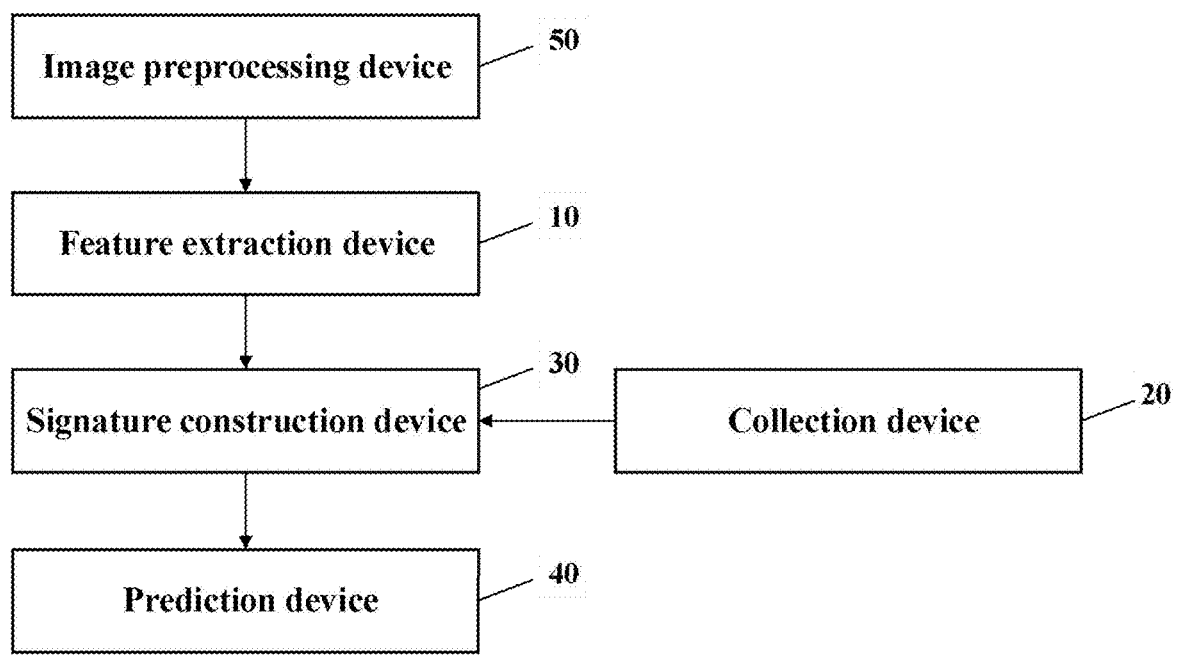
FIG. 2 depicts a block diagram of Example 2 of the system for predicting therapy resistance and its molecular mechanisms in rectal cancer before treatment according to the present disclosure.

Referring to FIG. 2, FIG. 2 is a block diagram of Example 2 of the system for predicting therapy resistance and its molecular mechanisms in rectal cancer before treatment according to the present disclosure.

On the basis of aforesaid Example 1, the system for predicting therapy resistance and its molecular mechanisms in rectal cancer before treatment in this example further comprises an image preprocessing device 50. The image preprocessing device 50 is used to invoke the radiological images having filtered and normalized signal intensity and stained pathological images of rectal biopsy specimens of the patient through a preset invoking path; the image preprocessing device 50 is further used to outline the radiological images and pathological images by ITK-SNAP software and ImageScope software so as to obtain the radiological images and pathological images marked with the region of interest of the patient.

In this example, the preset invoking path can be a invoking path provided by user, such as an access path of a memory disk of computer, or other devices that can store and invoke rectal MM and WSI images, which are not limited in this Example. After rectal MIll radiological images and WSI pathological images are uploaded by user, the rectal MIll radiological images are filtered through a filter and normalized for signal intensity to obtain the rectal MIll radiological images of the patient. The WSI pathological specimens of rectal biopsy were processed by hematoxylin-eosin staining to obtain the WSI pathological images of the patient.

In a specific example, ITK-SNAP (www.itksnap.org) is a medical image visualization software. After retrieving the patent's processed radiological images and pathological images, the image preprocessing device 50 outlines the region of interest (ROI) representing tumor tissue in the rectal MRI radiological images through ITK-SNAP software so as to obtain the radiological images marked with the region of interest of the patient. The radiological images marked with the region of interest of the patient refer to images in which a region of interest representing tumor tissue is marked. ImageScope (www.leicabiosystems.com) is a software for image browsing and editing. Users can use ImageScope (www.leicabiosystems.com) to adjust and enlarge, pan or zoom images, mark regions of interest, compare different stains, and analyze images among other functions. The image preprocessing device 50 also uses ImageScope (www.leicabiosystems.com) to outline the region of interest representing the tumor tissue in the WSI pathological images so as to obtain the pathological images marked with the region of interest of the patient.

It should be understood that, when outlining the radiological images and the pathological images, a professional clinician could use the image preprocessing device 50 to outline the radiological images and the pathological images.

In this example, the feature extraction device 10 is further used to extract features on the radiological images marked with the region of interest of the patient, at least based on first-order features, shape features and texture features for describing a lesion, thereby obtaining radiomics feature values. The feature extraction device 10 is further used to extract features on the pathological images marked with the region of interest of the patient, at least based on pixel intensity, morphological features and nuclear texture features, thereby obtaining pathomics feature values.

Pyradiomics (version 2.1.1, https://github.com/Radiomics/pyradiomics) is a feature extraction software platform that can extract radiomics features from medical images. In a specific example, the feature extraction device 10 uses Pyradiomics (version 2.1.1, https://github.com/Radiomics/pyradiomics) to extract features on the radiological images marked with the region of interest of the patient, to extract features on the radiological images marked with the region of interest of the patient, at least based on first-order features, shape features and texture features for describing a lesion, thereby obtaining radiomics feature values. The radiomics feature values contain at least 707 feature values, which are 19 first-order feature values describing a lesion, 16 shape feature values and 672 texture feature values. Among them, 672 texture feature values include 28 gray-level co-occurrence matrix (GLCM) feature values, 16 gray-level run-length matrix (GLRLM) feature values, 16 gray-level size zone matrix (GLSZM) feature values, 18 gray-level dependence matrix (GLDM) feature values, 269 Wavelets feature values and 325 Logs feature values. CellProfiler (version2.2.1, https://cellprofiler.org/) is a software platform for biological image processing. The feature extraction device 10 could also use CellProfiler software platform (version2.2.1, https://cellprofiler.org/) to extract features on the pathological images marked with the region of interest of the patient, to extract features on the pathological images marked with the region of interest of the patient, at least based on pixel intensity, morphological features and nuclear texture features, thereby obtaining pathomics feature values. The pathomics feature values contain at least 707 feature values, which include 175 pixel intensity feature values, 285 morphological feature values and 360 nuclear texture feature values.

In this example, the system for predicting therapy resistance and its molecular mechanisms in rectal cancer before treatment is supplemented with an image preprocessing device. The image preprocessing device is used to invoke the radiological images having filtered and normalized signal intensity and stained pathological images of rectal biopsy specimens of the patient through a preset invoking path. The image preprocessing device is further used to outline the radiological images and pathological images through ITK-SNAP software and ImageScope software so as to obtain the radiological images and pathological images marked with the region of interest of the patient. By preprocessing radiological images and pathological images with the image preprocessing device, the present disclosure could carry out in-depth mining for the information on radiological images and pathological images of the patient so as to extract features from radiological images and pathological images more accurately and improve the performance of prediction.

Figure 3:
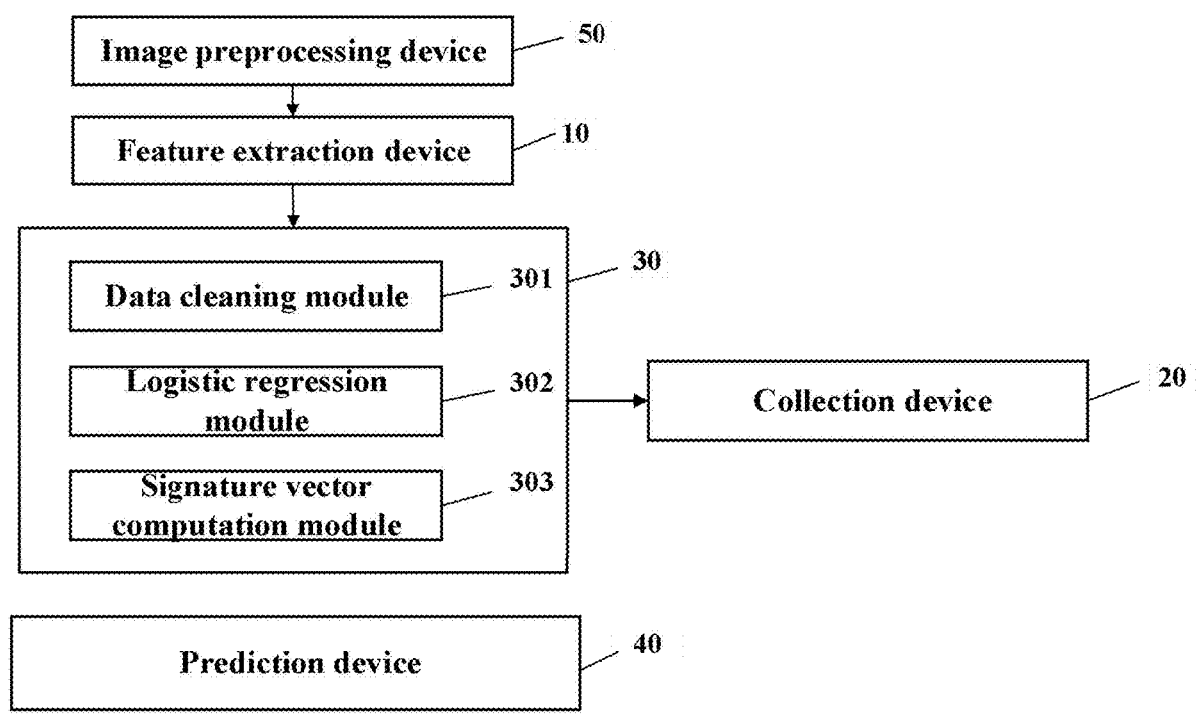
FIG. 3 depicts a block diagram of Example 3 of the system for predicting therapy resistance and its molecular mechanisms in rectal cancer before treatment according to the present disclosure.

Referring to FIG. 3, FIG. 3 is a block diagram of Example 3 of the system for predicting therapy resistance and its molecular mechanisms in rectal cancer before treatment according to the present disclosure.

On the basis of aforesaid Example 1 and Example 2, the signature construction device 30 in this Example further includes a data cleaning module 301, a logistic regression module 302 and a signature vector computation module 303. The data cleaning module 301 is used to clean multi-omics data of the radiomics feature values and the pathomics feature values to obtain the multi-omics data that meet the requirements by removing invalid data and erroneous data, and then to convert continuous variables in the multi-omics data into binary variables with the median as threshold to obtain converted multi-omics data.

In a specific example, the signature construction device 30 performs screening mainly based on the radiomics feature values and pathomics feature values input by the feature extraction device 10, then constructs multi-omics signatures of analysis of representative molecular markers characterizing three NCRT resistance mechanisms. It is mainly divided into three modules to operate. The first module is the data cleaning module 301, the multi-omics data of radiomics feature values and pathomics feature values input by the feature extraction device 10 are cleaned through the data cleaning module 301 to obtain valid multi-omics data that meet the requirements by removing invalid data and erroneous data in multi-omics data of radiomics feature values and pathomics feature values. The data cleaning module 301 is further used to convert continuous variables in the obtained multi-omics data that meet the requirements into binary variables with the median as threshold so as to obtain converted multi-omics data.

In this example, after the converted multi-omics data is obtained, the multi-omics data could be screened for dimensionality reduction through a logistic regression module 302. The logistic regression module 302 is used to perform dimensionality reduction on the converted multi-omics data based on the relationship between the omics features and the expression variables of the molecular markers, thereby obtaining radiomics features and pathomics features that can characterize the expression levels of the molecular markers and preset state.

It should be understood that, the relationship between the omics features and the expression variables of the molecular markers can be obtained from the molecular marker testing information in the clinical data of patients collected by the collection device 20. Dimensionality reduction is performed on the converted multi-omics data through the relationship between the omics features and the expression variables of the molecular markers. Specifically, the logistic regression module 302 is further used to perform dimensionality reduction on the converted multi-omics data through least absolute shrinkage and selection operator in R-language based on the relationship between the omics features and the expression variables of the molecular markers so as to screen out the radiomics features and pathomics features that can characterize the expression levels of the molecular markers and whether they are in deficient mismatch repair status.

R language (version 3.5.1; http://www.Rproject.org) is a software for data processing, computing and graphing. The logistic regression module 302 performs dimensionality reduction on the more than 2,000 omics variables in the converted multi-omics data through the least absolute shrinkage and selection operator in R-language (version 3.5.1; http://www.Rproject.org) so as to obtain the radiomics features and pathomics features that can significantly characterize the expression levels of four molecular markers HIF-1a, VEGF, CD4 and CD8 and whether they are in deficient mismatch repair status. The conditions for judging whether the expression levels of the above four molecular markers are significantly characterized are that the omics variables are higher or lower than the set threshold.

In a specific example, the logistic regression module 302 is further used to verify the screened radiomics features and pathomics features that can characterize the expression levels of molecular markers and whether they are in deficient mismatch repair status based on the molecular marker testing information and surgical pathological TRG information.

It should be noted that, the logistic regression module verifies the screened radiomics features and pathomics features that can characterize the expression levels of molecular markers and whether they are in deficient mismatch repair status by retrieving the molecular marker testing information and surgical pathological TRG information in the clinical data of patents so as to obtain more accurate radiomics features and pathomics features that significantly characterize the expression levels of four molecular markers HIF-1α, VEGF, CD4 and CD8 and whether they are in DMMR state according to the verification results. After the radiomics features and pathomics features are obtained, these features are computed by a signature vector computation module 303, which is used to perform machine learning with the radiomics features and pathomics features that can characterize the expression levels of each molecular marker and preset state so as to obtain corresponding radiomics feature vectors and pathomics feature vectors, and then to label the corresponding radiomics feature vectors and pathomics feature vectors to obtain multi-omics signatures characterizing therapy resistance and its molecular mechanisms.

In a specific example, the signature vector computation module 303 performs machine learning with the radiomics features and pathomics features that can characterize the expression levels of each molecular marker and preset state. The method of machine learning can be a decision tree method, a random forest method or other methods machine learning can be done, which are not limited in this example. The module 303 obtains the corresponding radiomics feature vectors and pathomics feature vectors among multi-omics feature vectors characterizing each molecular marker through machine learning, and then incorporate the multi-omics feature vectors characterizing each molecular marker into vector formula for computing and labeling so as to obtain multi-omics signatures that can characterize therapy resistance and its molecular mechanisms more accurately, including SigHif-1α, SigVEGF, SigCD4, SigCD8, and SigdMMR.

In this example, the signature construction device is configured to include a data cleaning module, a logistic regression module, and a signature vector computation module. The data cleaning module is used to clean multi-omics data of the radiomics feature values and the pathomics feature values so as to obtain multi-omics data that meet the requirements by removing invalid data and erroneous data, and then to convert continuous variables in the multi-omics data into binary variables with the median as threshold to obtain converted multi-omics data. The logistic regression module is used to perform dimensionality reduction on the converted multi-omics data based on the relationship between the omics features and the expression variables of the molecular markers, thereby obtaining radiomics features and pathomics features that can characterize the expression levels of the molecular markers and preset state. The signature vector computation module is used to perform machine learning with the radiomics features and pathomics features that can characterize the expression levels of each molecular marker and preset state so as to obtain corresponding radiomics feature vectors and pathomics feature vectors, and then to label the corresponding radiomics feature vectors and pathomics feature vectors to obtain multi-omics signatures characterizing therapy resistance and its molecular mechanisms. By using the data cleaning module, the data is cleaned so as to obtain valid data. By using the logistic regression module, the valid data is dimensionally reduced and screened to obtain data of radiomics features and pathomics features characterizing the expression levels of the molecular markers and preset state more accurately. By using the signature vector computation module, signatures of radiomics features and pathomics features characterizing the expression levels of the molecular markers and preset state are constructed to obtain multi-omics signatures that characterizes molecular typing more accurately.

Figure 4:
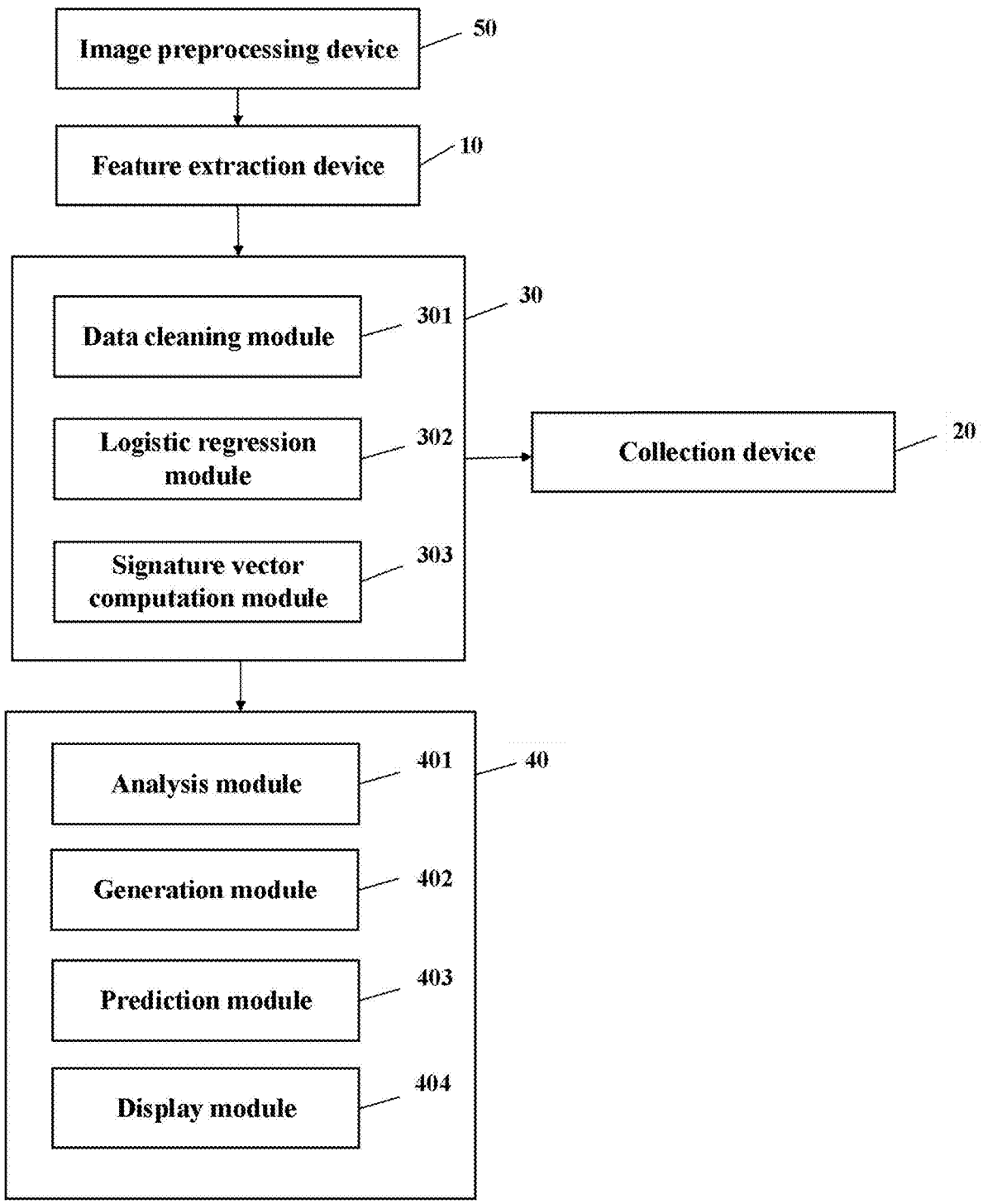
FIG. 4 depicts a block diagram of Example 4 of the system for predicting therapy resistance and its molecular mechanisms in rectal cancer before treatment according to the present disclosure.

Referring to FIG. 4, FIG. 4 is a block diagram of Example 4 of the system for predicting therapy resistance and its molecular mechanisms in rectal cancer before treatment according to the present disclosure.

On the basis of the aforesaid Example 1, the prediction device 40 in this example comprises an analysis module 401, a generation module 402 and a prediction module 403. The analysis module 401 is used to perform a univariable regression analysis on the clinical data and a multiple regression analysis on the multi-omics signatures characterizing therapy resistance and its molecular mechanisms, thereby obtaining clinical factors and molecular typing signatures that affect patient survival.

It should be understood that, the analysis module 401 screens out the clinical risk factors affecting the sensitivity of the patient to therapy resistance by using Univariable Regression Analysis in SPSS (Statistics 22; IBM Corp, Armonk, NY) software, and performs a multiple regression analysis on the multi-omics signatures characterizing therapy resistance and its molecular mechanisms by using Multiple Regression Analysis in SPSS (Statistics 22; IBM Corp, Armonk, NY) software, thereby obtaining clinical factors and molecular typing signatures that can independently affect patient survival.

The clinical risk factors affecting the sensitivity of the patient to therapy resistance refer to those factors that significantly and independently affect the sensitivity of the patient to therapy resistance, wherein TRG 1-2 is sensitive; TRG 3-4 is resistant. The clinical risk factors are factors with $P<0.05$, and P is probability of statistical hypothesis testing. The analysis module performs the multiple regression analysis on the multi-omics signatures characterizing therapy resistance and its molecular mechanisms by using Multiple Regression Analysis in SPSS (Statistics 22; IBM Corp, Armonk, NY) software, thereby obtaining molecular typing signatures that can significantly and independently affect patient survival.

Further, the generation module 402 is used to learn the clinical factors and molecular typing signatures that affect patient survival through an initial learning model so as to generate a prediction model; the prediction module 403 is used to predict the therapy resistance and its molecular mechanisms in rectal cancer based on the input pathological information to be predicted.

It should be noted that, the initial learning model can be a machine learning model obtained by learning through decision tree, random forest, support vector machines, Naive Bayes or other methods machine learning can be done. The molecular typing signatures and clinical factors obtained by the analysis module 401 that significantly and independently affect patient survival are input into the initial learning model for learning so as to generate a prediction model. The prediction model refers to a model for sensitivity to therapy resistance with high accuracy and stability. After the prediction model is generated, the prediction module 403 receives prospective pathological information to be predicted that is input subsequently by the operator, and inputs it into the prediction model for prediction. The prospective pathological information to be predicted includes the MRI images, WSI images, and clinical data of patients. Through the prediction model, the therapy resistance and its molecular mechanisms in rectal cancer are predicted based on the input pathological information to be predicted, and prediction results are obtained, thereby simultaneous prediction of NCRT resistance and underlying molecular mechanisms in LARC patients before treatment is enabled.

Moreover, the prediction device 40 further comprises a display module 404. The display module 404 is used to display prediction results through alignment diagram and to display weights of the corresponding molecular typing signatures and probability of therapy resistance in rectal cancer.

The display module 404 is used to display the results predicted by the prediction model. By generating a structural alignment diagram and a receiver operating characteristic (ROC) curve representing prediction performance of the model based on model training or validation cases set, module 404 displays prediction results. By using the alignment diagram to display weights of the corresponding molecular typing signatures, namely the alignment diagram scores and to display probability of NCRT resistance, namely the total scores of the model and the corresponding probability, module 404 could achieve simultaneous prediction of NCRT resistance and underlying molecular mechanisms in LARC patients before treatment.

Figure 5:
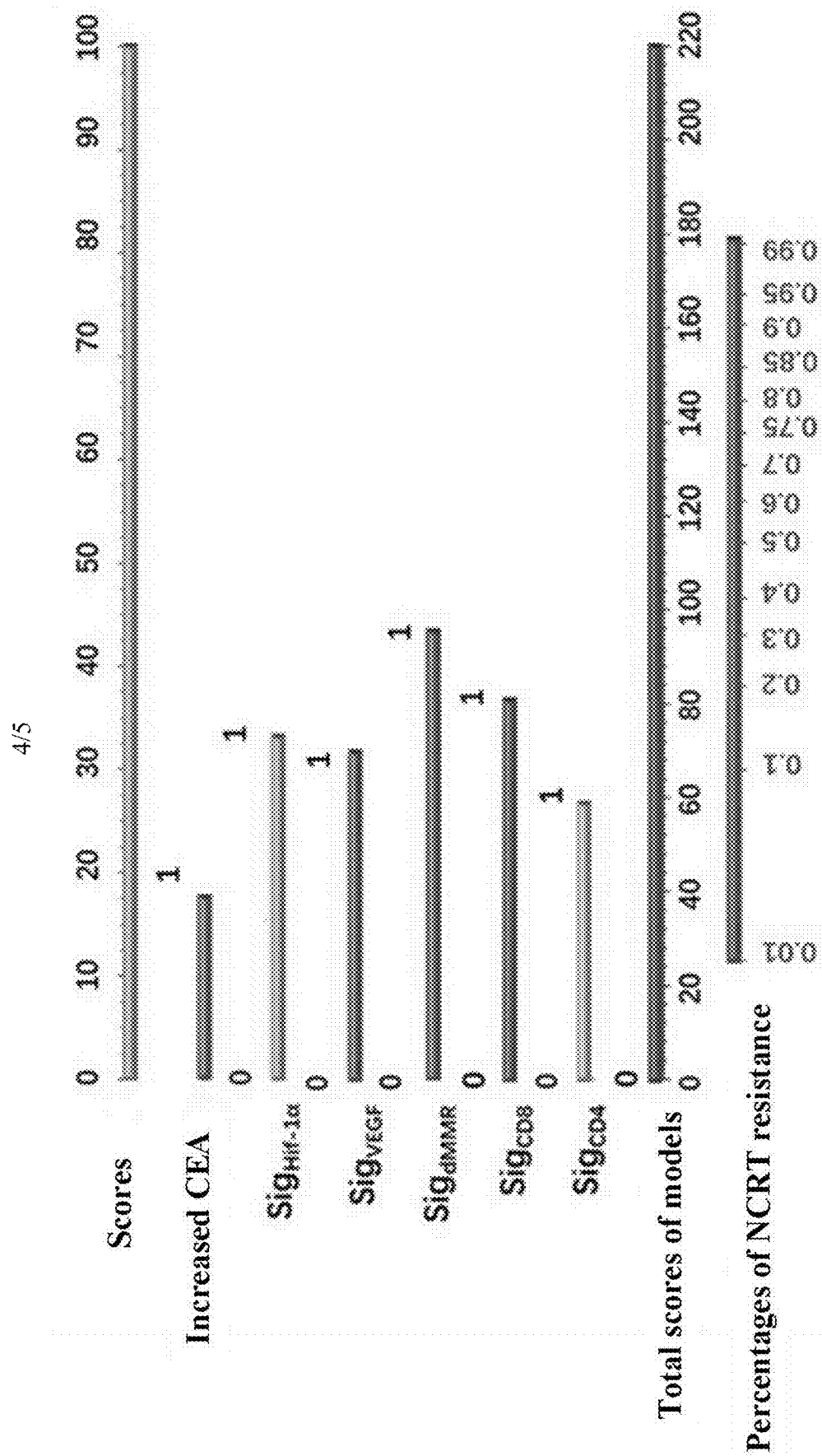
FIG. 5 depicts an alignment diagram displayed by the display module in an example of the system for predicting therapy resistance and its molecular mechanisms in rectal cancer before treatment according to the present disclosure.

Further, the aforesaid predicting device 40 will be described in detail by a specific example. Taking a situation including clinical data, MM images and WSI images of 358 LARC patients as an example to illustrate the construction and external verification of the system for predicting therapy resistance and its molecular mechanisms in rectal cancer before treatment. The patients were sorted based on the time of treatment and divided into a training group of 250 cases and an external verification group of 108 cases in a ratio of 7:3. The Mill and biopsy pathological WSI images of the patients in the training group were stored into a predetermined folder, complete information of the patients is input into the collection device 20. After the above model construction process of system, the alignment diagram shown in FIG. 5 is finally displayed in the display module 404. In FIG. 5, the scores are the alignment diagram scores for each molecular typing signatures. The signatures for molecular typing packages include: CEA, SigHif-1α, SigVEGF, SigdMMR, SigCD4, and SigCD8. The weights of each molecular typing label, as well as NCRT resistance rate, that is, the total scores of the model and the corresponding probability are showed.

Figure 6:
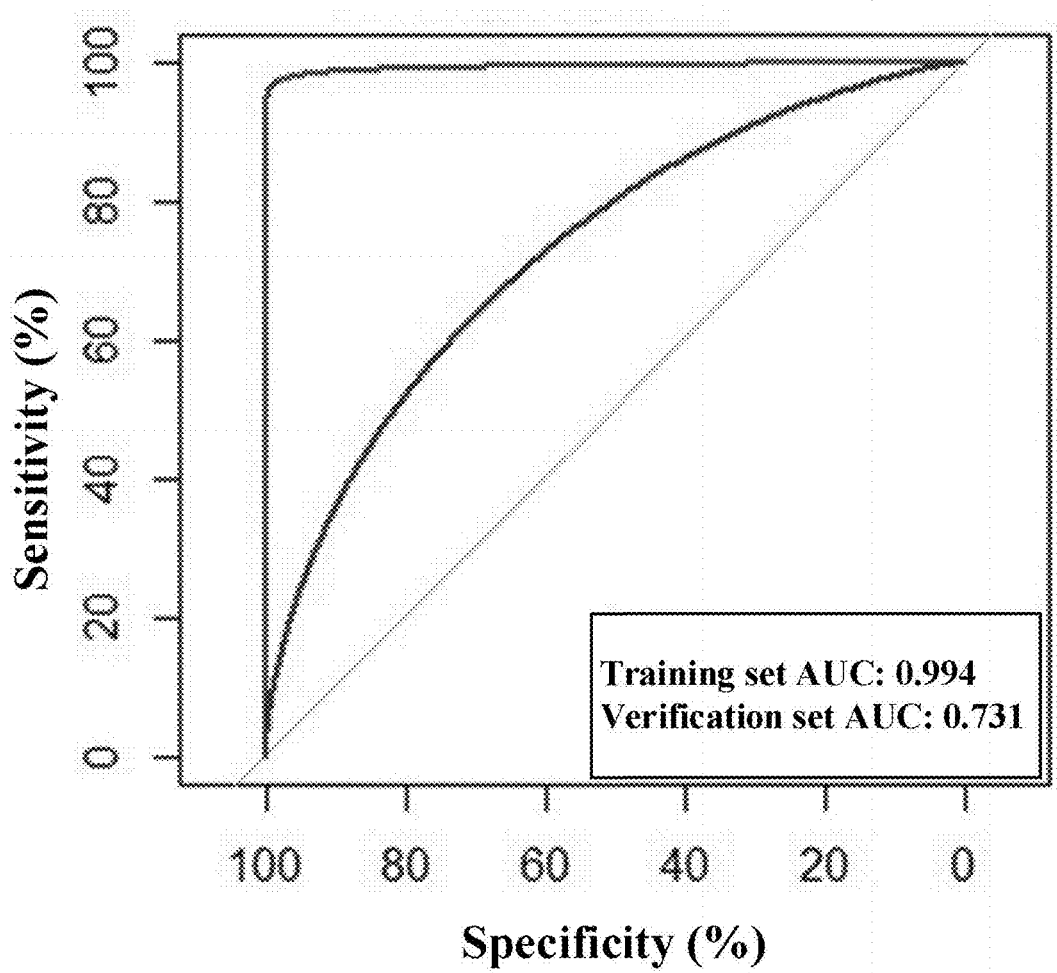
FIG. 6 depicts a schematic diagram of prediction performance of the prediction model on cases in a training set and cases in a verification set in an example of the system for predicting therapy resistance and its molecular mechanisms in rectal cancer before treatment according to the present disclosure.

After completing the construction of the initial system model, the MM images, WSI images and clinical data (no molecular testing information and pathological information in the clinical data) in verification cases are input in sequence, the system could compute based on the aforesaid alignment diagram and display the scores for each molecular label and percentages of NCRT resistance for a specific patient, and give a prediction of therapy resistance and its molecular mechanisms. After the patients to be predicted are used as verification cases and all the prediction results are produced, the actual molecular expression and pathological TRG response are input into the system, and the consistency and stability of the model are evaluated based on the deviation between the prediction and the actual situation. As shown in FIG. 6, FIG. 6 is a graph showing the prediction performance of the prediction model used by the system for predicting therapy resistance and its molecular mechanisms in rectal cancer before treatment according to the present disclosure on cases in a training set and cases in a verification set, wherein the horizontal axis represents the percentage of specificity, and the vertical axis represents the percentage of sensitivity, where areas under curve (AUC, the area under the ROC curve) are up to 0.994 and 0.731 respectively.

In this example, the prediction device is configured to include an analysis module, a generation module, and a prediction module. The analysis module is used to perform a univariable regression analysis on the clinical data and to perform a multiple regression analysis on the multi-omics signatures characterizing therapy resistance and its molecular mechanisms, thereby obtaining clinical factors and molecular typing signatures that affect patient survival. The generation module is used to learn the clinical factors and molecular typing signatures that affect patient survival through an initial learning model so as to generate a prediction model. The prediction module is used to predict the therapy resistance and its molecular mechanisms in rectal cancer based on the input information to be predicted (such as pathological information) through the prediction model, enabling simultaneous prediction of NCRT resistance and underlying molecular mechanism in LARC patients before treatment.

It should be understood that, the above examples are only for illustration, and do not constitute any limitation to the technical solution of the present disclosure. In specific applications, those skilled in the art could make settings as needed, not be limited by the present disclosure.

It should be noted that, the workflows described above are only illustrative and will not limit the protection scope of the present disclosure. In practical applications, those skilled in the art could select some or all of them according to actual needs to achieve the purpose of the technical solution in Examples, and there is no limitation here.

In addition, regarding the technical details not described in detail in the Examples, those skilled in the art may refer to the system for predicting therapy resistance and its molecular mechanisms in rectal cancer before treatment provided by any example of the present disclosure, more details are not described repeatedly here.

In addition, it should be noted that, the terms "comprise", "include" or any other variations thereof herein are intended to be inclusive such that a process, method, item or system comprising a series of elements includes not only those listed elements, but also includes additional elements not clearly listed, or also includes elements inherent in such a process, method, item or system. Without further limitations, an element defined by the phrase "comprising a . . . " does not exclude the presence of additional identical elements in the process, method, item or system comprising that element.

The serial numbers of the above examples according to the present disclosure are only for description, and do not mean that the examples are superior or inferior.

With the help of the above description of the mode for carrying out the present application, those skilled in the art could clearly understand that the systems of the above examples could be realized by means of software plus a necessary general-purpose hardware platform, of course, it could also be realized by hardware, but in many cases the former is a better solution.

The above only provides optional examples of the present disclosure, not to limit the scope of the present disclosure. Any equivalent changes on structure and process made by using the specification and the accompanying drawings of the present disclosure, or direct/indirect applications in other related technical fields are all included in the protection scope of the present disclosure in the same way.

What is claimed is:

1. A system for predicting therapy resistance and its molecular mechanisms in rectal cancer before treatment, wherein the system comprises an image preprocessing device, a feature extraction device, a collection device, a signature construction device and a prediction device;

the image preprocessing device is configured to invoke radiological images having filtered and normalized signal intensity and stained pathological images of rectal biopsy specimens through a preset invoking path and the image preprocessing device is further configured to outline the radiological images and pathological images by ITK-SNAP software and ImageScope software to obtain the radiological images and pathological images marked with the region of interest of the patient;

the feature extraction device is configured to extract features on the radiological images and the pathological images marked with a region of interest of a patient, thereby obtaining radiomics feature values and pathomics feature values;

the collection device is configured to collect clinical data of the patient;

the signature construction device is configured to screen radiomics feature values and pathomics feature values, and then to construct multi-omics signatures characterizing therapy resistance and molecular mechanism thereof;

the prediction device is configured to perform regression analysis on the multi-omics signatures characterizing therapy resistance and molecular mechanism thereof and the clinical data, and then to display prediction results of therapy resistance and its molecular mechanisms in rectal cancer based on analysis results;

the signature construction device comprises a data cleaning module, a logistic regression module, and a signature vector computation module;

the data cleaning module comprises executable code, stored in non-transitory storage, which when executed is configured to clean multi-omics data of the radiomics feature values and the pathomics feature values to obtain the multi-omics data that meet requirements by removing invalid data and erroneous data, and then to convert continuous variables in the multi-omics data into binary variables with the median as threshold to obtain converted multi-omics data;

the logistic regression module comprises executable code, stored in the non-transitory storage, which when executed is configured to perform dimensionality reduction on the converted multi-omics data based on a relationship between the omics features and the expression variables of the molecular markers, so as to obtain radiomics features and pathomics features that can characterize the expression levels of the molecular markers and preset state; and the signature vector computation module comprises executable code, stored in the non-transitory storage, which when executed is configured to perform machine learning with the radiomics features and pathomics features that can characterize the expression levels of each molecular marker and preset state so as to obtain corresponding radiomics feature vectors and pathomics feature vectors, and then to label the corresponding radiomics feature vectors and pathomics feature vectors so as to obtain multi-omics signatures characterizing treatment resistance and its molecular mechanism, wherein the prediction device comprises at least one computer processor, a display, and a prediction module, the prediction module comprises executable code stored in the non-transitory storage which when executed, by the at least one computer processor, is configured to predict the therapy resistance and its molecular mechanisms in rectal cancer based on input pathological information to be predicted, wherein the prediction device further comprises a display module, the display module comprising executable code, stored in the non-transitory storage, which when executed is configured to display, using the display, prediction results through an alignment diagram, and to display weights of the corresponding molecular typing signatures and probability of therapy resistance in rectal cancer.

2. The system for predicting therapy resistance and its molecular mechanisms in rectal cancer before treatment according to claim 1, wherein the feature extraction device is further configured to extract features on the radiological images marked with the region of interest of the patient, at least based on first-order features, shape features and texture features for describing a lesion, so as to obtain radiomics feature values; and the feature extraction device is further configured to extract features on the pathological images marked with the region of interest of the patient, at least based on pixel intensity, morphological features and nuclear texture features, so as to obtain pathomics feature values.

3. The system for predicting therapy resistance and its molecular mechanisms in rectal cancer before treatment according to claim 1, wherein the collection device is further configured to invoke an information collection platform, and to collect information at least comprising gender, age, body mass index, tumor differentiation degree, serological test results, molecular marker testing information and surgical pathological tumor regression grade information; and the collection device is further configured to obtain clinical data of patients based on the information comprising gender, age, body mass index, the tumor differentiation degree, serological test results, molecular marker testing information and surgical pathological tumor regression grade information.

4. The system for predicting therapy resistance and its molecular mechanisms in rectal cancer before treatment according to claim 1, wherein the logistic regression module is further comprises stored executable code configured to perform dimensionality reduction on the converted multi-omics data through least absolute shrinkage and selection operator in R-language based on the relationship between the omics features and the expression variables of the molecular markers so as to screen out the radiomics features and pathomics features that can characterize the expression levels of the molecular markers and whether they are in deficient mismatch repair status.

5. The system for predicting therapy resistance and its molecular mechanisms in rectal cancer before treatment according to claim 1, wherein the logistic regression module is further comprises stored executable code configured to verify the screened radiomics features and pathomics features that can characterize the expression levels of molecular markers and whether they are in deficient mismatch repair status based on the molecular marker testing information and surgical pathological tumor regression grade information.

6. The system for predicting therapy resistance and its molecular mechanisms in rectal cancer before treatment according to claim 1, wherein the prediction device comprises an analysis module and a generation module;

the analysis module comprises executable code, stored in non-transitory storage, which when executed is configured to perform a univariable regression analysis on the clinical data and a multiple regression analysis on the multi-omics signatures characterizing therapy resistance and molecular mechanism thereof, thereby obtaining clinical factors and molecular typing signatures that affect patient survival; and the generation module comprises executable code, stored in the non-transitory storage, which when executed is configured to learn the clinical factors and molecular typing signatures that affect patient survival through an initial learning model so as to generate a prediction model.

7. The system for predicting therapy resistance and its molecular mechanisms in rectal cancer before treatment according to claim 6, wherein the analysis module further comprises stored executable code configured to screen out clinical risk factors affecting sensitivity to therapy resistance in patients by the univariable regression analysis in SPSS software, and to perform the multiple regression analysis on the multi-omics signatures that characterize therapy resistance and molecular mechanism thereof using the multiple regression analysis in SPSS software, so as to obtain clinical factors and molecular typing signatures that can independently affect patient survival.

* * * * *